United States Patent
Leung et al.

(10) Patent No.: US 10,682,188 B2
(45) Date of Patent: Jun. 16, 2020

(54) SYSTEMS AND METHODS FOR INTRAOPERATIVE SPINAL LEVEL VERIFICATION

(71) Applicant: 7D SURGICAL INC., Toronto (CA)

(72) Inventors: Michael K. K. Leung, Markham (CA); Adrian Mariampillai, Toronto (CA); Beau Anthony Standish, Toronto (CA); Peter Siegler, Toronto (CA); Victor X. D. Yang, North York (CA)

(73) Assignee: 7D SURGICAL INC., Toronto, ON (CA)

( * ) Notice: Subject to any disclaimer, the term of this patent is extended or adjusted under 35 U.S.C. 154(b) by 15 days.

(21) Appl. No.: 16/304,604

(22) PCT Filed: Jun. 23, 2017

(86) PCT No.: PCT/CA2017/050770
§ 371 (c)(1),
(2) Date: Nov. 26, 2018

(87) PCT Pub. No.: WO2017/219149
PCT Pub. Date: Dec. 28, 2017

(65) Prior Publication Data
US 2019/0298456 A1    Oct. 3, 2019

Related U.S. Application Data

(60) Provisional application No. 62/353,886, filed on Jun. 23, 2016.

(51) Int. Cl.
*A61B 34/20* (2016.01)
*A61B 34/10* (2016.01)
(Continued)

(52) U.S. Cl.
CPC .............. *A61B 34/20* (2016.02); *A61B 17/56* (2013.01); *A61B 34/10* (2016.02); *G06T 7/0012* (2013.01);
(Continued)

(58) Field of Classification Search
CPC .............. A61B 34/10; A61B 2034/105; A61B 2034/107; A61B 34/20; A61B 2034/2055;
(Continued)

(56) References Cited

U.S. PATENT DOCUMENTS 9,119,670 B2   9/2015  Yang et al.
2008/0063301 A1  3/2008  Bogoni et al.
(Continued)

FOREIGN PATENT DOCUMENTS

CA    2961079 A1 *  3/2016  ............. A61B 17/88
CA    2961079 A1    3/2016
(Continued)

OTHER PUBLICATIONS

International Search Report for the parent PCT application PCT/CA2017/050770, dated Oct. 31, 2017.
(Continued)

*Primary Examiner* — Larry E Waggle, Jr.
(74) *Attorney, Agent, or Firm* — Hill & Schumacher

(57) ABSTRACT

Systems and methods are provided in which intraoperatively acquired surface data is employed to verify the correspondence of an intraoperatively selected spinal level with a spinal level that is pre-selected based on volumetric image data. Segmented surface data corresponding to the pre-selected spinal levels may be obtained from the volumetric image data, such that the segmented surface data corresponds to a spinal segment that is expected to be exposed and identified intraoperatively during the surgical procedure. The segmented surface data from the pre-selected spinal (Continued)

level, and adjacent segmented surface data from an adjacent spinal level that is adjacent to the pre-selected spinal level, is registered to the intraoperative surface data, and quality measures associated with the registration are obtained, thereby permitting an assessment or a determination of whether or not the pre-selected spinal surface (in the volumetric frame of reference) is likely to correspond to the intraoperatively selected spinal level.

28 Claims, 12 Drawing Sheets

(51) Int. Cl.
| | |
|---|---|
| G06T 7/38 | (2017.01) |
| G06T 7/10 | (2017.01) |
| G06T 7/11 | (2017.01) |
| A61B 17/56 | (2006.01) |
| G06T 7/00 | (2017.01) |
| G06T 7/168 | (2017.01) |
| G06T 7/262 | (2017.01) |
| A61B 90/00 | (2016.01) |
| A61B 17/00 | (2006.01) |

(52) U.S. Cl.
CPC .................. *G06T 7/10* (2017.01); *G06T 7/11* (2017.01); *G06T 7/168* (2017.01); *G06T 7/262* (2017.01); *G06T 7/38* (2017.01); *A61B 2017/00115* (2013.01); *A61B 2017/564* (2013.01); *A61B 2034/2055* (2016.02); *A61B 2034/2065* (2016.02); *A61B 2090/363* (2016.02); *A61B 2090/364* (2016.02)

(58) Field of Classification Search
CPC ...... A61B 2034/2065; A61B 2090/363; A61B 2090/364; A61B 2576/02; G06T 7/0012; G06T 7/10; G06T 7/11; G06T 7/136; G06T 7/168; G06T 7/187; G06T 7/262; G06T 2207/30012; G06T 7/33; G06T 7/35; G06T 7/38

See application file for complete search history.

(56) References Cited

U.S. PATENT DOCUMENTS

| | | |
|---|---|---|
| 2010/0054525 A1 | 3/2010 | Gong et al. |
| 2013/0060146 A1 | 3/2013 | Yang et al. |

FOREIGN PATENT DOCUMENTS

| | | |
|---|---|---|
| WO | 2011134083 A1 | 11/2011 |
| WO | 2015074158 A1 | 5/2015 |
| WO | 2016044934 A1 | 3/2016 |

OTHER PUBLICATIONS

Irace, C., "Intraoperative Imaging for Verification of the Correct Level During Spinal Surgery". Chapter 9 from Novel Frontiers of Advanced Neuroimaging, Edited by Kostas N. Fountas, Jan. 9, 2013.

Herring, Jeannette and Benoit Dawant, "Automatic Lumbar Vertebral Identification Using Surface-Based Registration" Journal of Biomedical Informatics 34, 74-87, (2001).

Hartkens, Thomas, "Intraoperative Spine Segment Guidance System", Prior Art Publishing, Prior Art Journal 2014 #02, pp. 226-227 Feb. 3, 2014.

\* cited by examiner

WARNING!

Please verify points were selected on correct spinal level. Better match was identified one level above.

| Return to Registration | Proceed to Navigation |

FIG. 4A

SYSTEMS AND METHODS FOR INTRAOPERATIVE SPINAL LEVEL VERIFICATION

CROSS-REFERENCE TO RELATED APPLICATION

This application is a National Phase application claiming the benefit of the international PCT Patent Application No. PCT/CA2017/050770, filed on Jun. 23, 2017, in English, which claims priority to U.S. Provisional Application No. 62/353,886, titled "SYSTEMS AND METHODS FOR INTRAOPERATIVE SPINAL LEVEL VERIFICATION" and filed on Jun. 23, 2016, the entire contents of which are incorporated herein by reference.

BACKGROUND

The present disclosure relates to image-guided surgical navigation. More particularly, the present disclosure relates to image-guided surgical navigation of spinal procedures using intraoperative surface detection.

A common problem in image-guided surgery of the spine is to correctly associate fiducials selected in volumetric image data of the patient with the fiducials intraoperatively selected on the patient for intraoperative registration. In procedures related to the spine, these fiducials are usually associated with a spinal level, which means that the surgeon must correctly locate the spinal level intraoperatively on the patient from which corresponding fiducials have been selected in the volumetric image data. This is often difficult, and as a result, surgeons are often required to check which spinal levels to operate on using imaging modalities involving X-rays to obtain a view of the spine beyond what's visible from the surgical incision.

SUMMARY

Systems and methods are provided in which intraoperatively acquired surface data is employed to verify the correspondence of an intraoperatively selected spinal level with a spinal level that is pre-selected based on volumetric image data. Segmented surface data corresponding to the pre-selected spinal levels may be obtained from the volumetric image data, such that the segmented surface data corresponds to a spinal segment that is expected to be exposed and identified intraoperatively during the surgical procedure. The segmented surface data from the pre-selected spinal level, and adjacent segmented surface data from an adjacent spinal level that is adjacent to the pre-selected spinal level, is registered to the intraoperative surface data, and quality measures associated with the registration are obtained, thereby permitting an assessment or a determination of whether or not the pre-selected spinal surface (in the volumetric frame of reference) is likely to correspond to the intraoperatively selected spinal level.

Accordingly, in a first aspect, there is provided a method of performing intraoperative spinal level verification, the method comprising:

obtaining volumetric image data pertaining to a plurality of spinal levels of a spine;

processing the volumetric image data to generate multi-level surface data characterizing a bone surface of the spine;

obtaining input identifying at least three volumetric fiducial points at a pre-selected set of one or more contiguous spinal levels within a volumetric frame of reference associated with the volumetric image data and the multi-level surface data;

obtaining directional information associated with an orientation of the spine in the volumetric frame of reference;

employing at least one of the volumetric fiducial points to perform segmentation on the multi-level surface data, thereby obtaining segmented surface data associated with the pre-selected set of one or more contiguous spinal levels;

employing the directional information to determine an adjacent volumetric region within the volumetric frame of reference that is associated with an adjacent set of one or more contiguous spinal levels that is adjacent to the pre-selected set of one or more contiguous spinal levels;

performing segmentation on the multi-level surface data within the adjacent volumetric region, thereby obtaining adjacent segmented surface data associated with the adjacent set of one or more contiguous spinal levels;

registering the segmented surface data associated with the pre-selected set of one or more contiguous spinal levels to the adjacent segmented surface data, thereby obtaining an inter-level registration transform between the pre-selected set of one or more contiguous spinal levels and the adjacent set of one or more contiguous spinal levels;

intraoperatively detecting, with a surface detection subsystem, intraoperative surface data characterizing a surface region including at least a portion of an intraoperatively selected set of one or more contiguous spinal levels;

obtaining input identifying at least three intraoperative fiducial points associated with the intraoperatively selected set of one or more contiguous spinal levels, within an intraoperative frame of reference associated with the intraoperative surface data, each intraoperative fiducial point corresponding to a respective volumetric fiducial point;

employing the volumetric fiducial points and the corresponding intraoperative fiducial points to perform an initial registration between the segmented surface data and the intraoperative surface data, and performing a secondary surface-to-surface registration between the segmented surface data and the intraoperative surface data;

employing the inter-level registration transform to perform registration between the intraoperative surface data and the adjacent segmented surface data;

determining registration quality measures comprising:

a primary registration quality measure associated with a quality of the registration between the intraoperative surface data and the segmented surface data; and an adjacent registration quality measure associated with a quality of the registration between the intraoperative surface data and the adjacent segmented surface data associated with the adjacent set of one or more contiguous spinal levels; and providing feedback associated with the registration quality measures.

In another aspect, there is provided system for performing intraoperative spinal level verification, the system comprising:

a surface detection subsystem; and computer hardware operatively coupled to said surface detection subsystem, wherein said computer hardware comprises memory coupled with one or more processors to store instructions, which when executed by the one or more processors, causes the one or more processors to perform operations comprising:

processing volumetric image data pertaining to a plurality of spinal levels of a spine to generate multi-level surface data characterizing a bone surface of the spine;

receiving input identifying at least three volumetric fiducial points at a pre-selected set of one or more contiguous spinal levels within a volumetric frame of reference associated with the volumetric image data and the multi-level surface data;

obtaining directional information associated with an orientation of the spine in the volumetric frame of reference;

employing at least one of the volumetric fiducial points to perform segmentation on the multi-level surface data, thereby obtaining segmented surface data associated with the pre-selected set of one or more contiguous spinal levels;

employing the directional information to determine an adjacent volumetric region within the volumetric frame of reference that is associated with an adjacent set of one or more contiguous spinal levels that is adjacent to the pre-selected set of one or more contiguous spinal levels;

performing segmentation on the multi-level surface data within the adjacent volumetric region, thereby obtaining adjacent segmented surface data associated with the adjacent set of one or more contiguous spinal levels;

registering the segmented surface data associated with the pre-selected set of one or more contiguous spinal levels to the adjacent segmented surface data, thereby obtaining an inter-level registration transform between the pre-selected set of one or more contiguous spinal levels and the adjacent set of one or more contiguous spinal levels;

controlling said surface detection subsystem to intraoperatively detect intraoperative surface data characterizing a surface region including at least a portion of an intraoperatively selected set of one or more contiguous spinal levels;

receiving input identifying at least three intraoperative fiducial points associated with the intraoperatively selected set of one or more contiguous spinal levels, within an intraoperative frame of reference associated with the intraoperative surface data, each intraoperative fiducial point corresponding to a respective volumetric fiducial point;

employing the volumetric fiducial points and the corresponding intraoperative fiducial points to perform an initial registration between the segmented surface data and the intraoperative surface data, and performing a secondary surface-to-surface registration between the segmented surface data and the intraoperative surface data;

employing the inter-level registration transform to perform registration between the intraoperative surface data and the adjacent segmented surface data;

determining registration quality measures comprising:
a primary registration quality measure associated with a quality of the registration between the intraoperative surface data and the segmented surface data; and
an adjacent registration quality measure associated with a quality of the registration between the intraoperative surface data and the adjacent segmented surface data associated with the adjacent set of one or more contiguous spinal levels; and
providing feedback associated with the registration quality measures.

In another aspect, there is provided a method of performing intraoperative spinal level verification, the method comprising:
obtaining volumetric image data pertaining to a plurality of spinal levels of a spine;
processing the volumetric image data to generate multi-level surface data characterizing a bone surface of the spine;
performing segmentation on the multi-level surface data, thereby obtaining:
segmented surface data associated with a pre-selected set of one or more contiguous spinal levels; and
adjacent segmented surface data associated with an adjacent set of one or more contiguous spinal levels;
intraoperatively detecting, with a surface detection subsystem, intraoperative surface data characterizing a surface region including at least a portion of an intraoperatively selected set of one or more contiguous spinal levels;
performing registration between the intraoperative surface data and the segmented surface data;
performing registration between the intraoperative surface data and the adjacent segmented surface data;
determining registration quality measures comprising:
a primary registration quality measure associated with a quality of the registration between the intraoperative surface data and the segmented surface data; and
an adjacent registration quality measure associated with a quality of the registration between the intraoperative surface data and the adjacent segmented surface data associated with the adjacent set of one or more contiguous spinal levels; and
providing feedback associated with the registration quality measures.

In another aspect, there is provided a system for performing intraoperative spinal level verification, the system comprising:
a surface detection subsystem; and
computer hardware operatively coupled to said surface detection subsystem, wherein said computer hardware comprises memory coupled with one or more processors to store instructions, which when executed by the one or more processors, causes the one or more processors to perform operations comprising:
processing the volumetric image data pertaining to a plurality of spinal levels of a spine to generate multi-level surface data characterizing a bone surface of the spine;
performing segmentation on the multi-level surface data, thereby obtaining:
segmented surface data associated with a pre-selected set of one or more contiguous spinal levels; and
adjacent segmented surface data associated with an adjacent set of one or more contiguous spinal levels;
intraoperatively detecting, with a surface detection subsystem, intraoperative surface data characterizing a surface region including at least a portion of an intraoperatively selected set of one or more contiguous spinal levels;
performing registration between the intraoperative surface data and the segmented surface data;
performing registration between the intraoperative surface data and the adjacent segmented surface data;
determining registration quality measures comprising:
a primary registration quality measure associated with a quality of the registration between the intraoperative surface data and the segmented surface data; and
an adjacent registration quality measure associated with a quality of the registration between the intraoperative surface data and the adjacent segmented surface data associated with the adjacent set of one or more contiguous spinal levels; and
providing feedback associated with the registration quality measures.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which:

FIGS. 4A-C illustrate different example methods of providing feedback based on the registration quality measures.

DETAILED DESCRIPTION

Figure 1:
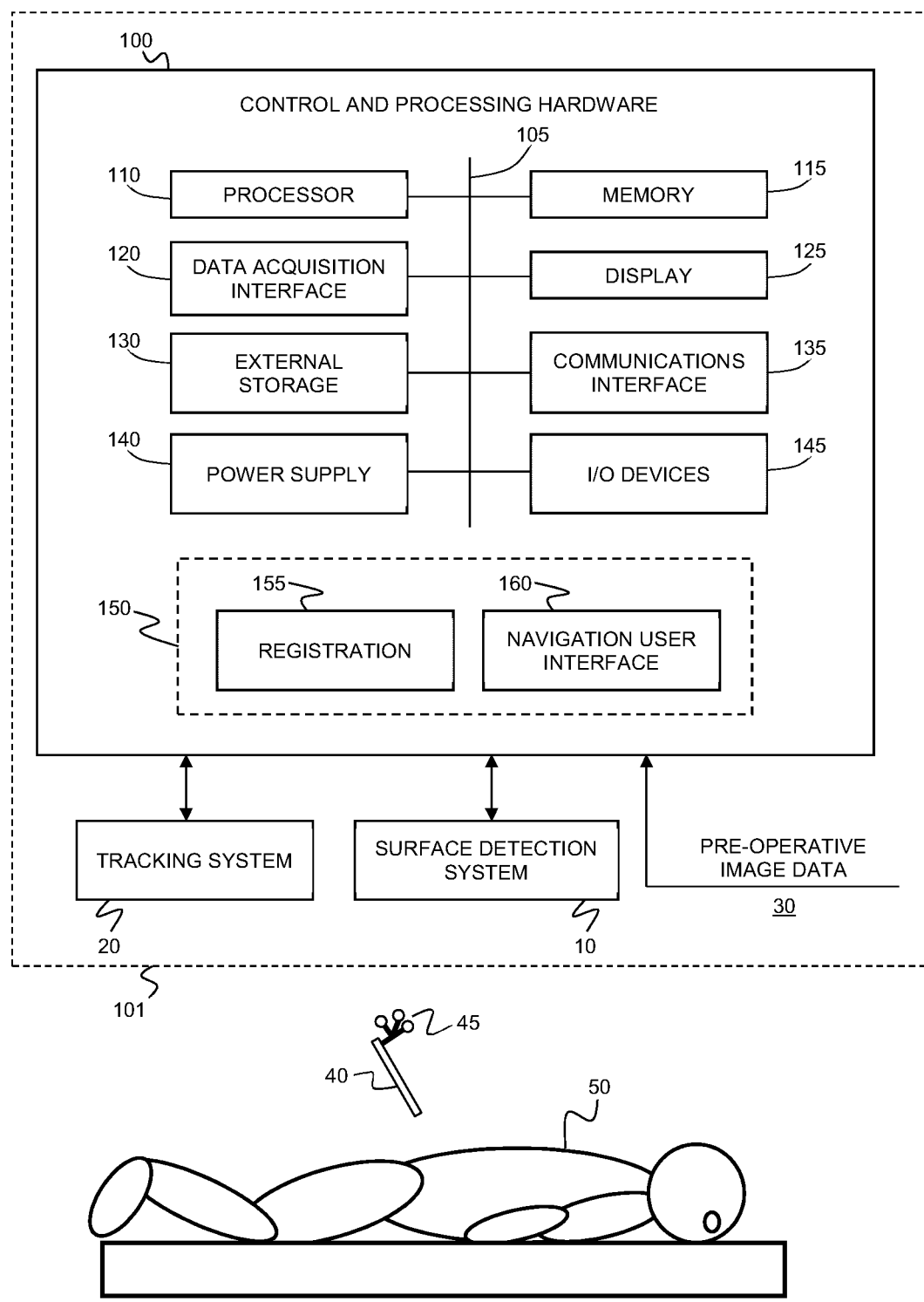
FIG. 1 shows an example system for performing intraoperative spine level verification.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. Unless otherwise specified, the terms "about" and "approximately" mean plus or minus 25 percent or less.

It is to be understood that unless otherwise specified, any specified range or group is as a shorthand way of referring to each and every member of a range or group individually, as well as each and every possible sub-range or sub-group encompassed therein and similarly with respect to any sub-ranges or sub-groups therein. Unless otherwise specified, the present disclosure relates to and explicitly incorporates each and every specific member and combination of sub-ranges or sub-groups.

As used herein, the term "on the order of", when used in conjunction with a quantity or parameter, refers to a range spanning approximately one tenth to ten times the stated quantity or parameter.

Various example embodiments of the present disclosure provide systems and methods for performing intraoperative spinal level verification during (or after) performing a spinal procedure. During a spinal procedure, one or more spinal levels are exposed intraoperatively. These spinal levels are henceforth referred to as intraoperative spinal levels. The intraoperative spinal levels that are exposed during the surgical procedure may be difficult to identify, since only a small subset of the spine is typically exposed, and since the surgical field of view is typically complicated by the presence of tissue and blood, thus presenting potential difficulty to the surgeon in identifying the exposed level(s). Although a surgeon may attempt to identify an intraoperatively exposed spinal level by counting spinal levels from landmarks that have been identified from preoperative volumetric image data (e.g. computed tomography), this is not always reliable, and is prone to human error. The practice is further complicated in cases in which patients have significant body fat or degenerative anatomy due to disease. As a result, intraoperative X-rays are frequently required, which allows the surgeon to visualize anatomical structures much deeper than the surgical exposure for spinal level confirmation. This increases the surgical time, and exposes the operating room staff and patient to ionizing radiation. It is readily apparent that the consequences of a misidentified spinal level, and the incorrect execution of a surgical plan, can have significant negative consequences for patient and the surgeon.

Various aspects of the present disclosure address this problem by providing solutions that employ a surface detection system to obtain intraoperative surface data characterizing the exposed surface of the spine. This intraoperative surface data may be compared with segmented surface data obtained from volumetric data of the spine.

In one example embodiment, segmented surface data is obtained from the volumetric image data, such that the segmented surface data corresponds to a pre-selected spinal segment that is expected to be exposed and identified intraoperatively during the surgical procedure. The segmented surface data from the pre-selected spinal level, and adjacent segmented surface data from an adjacent spinal level that is adjacent to the pre-selected spinal level, is registered to the intraoperative surface data, and quality measures associated with the registration are obtained, thereby permitting an assessment or a determination of whether or not the pre-selected spinal surface (in the volumetric frame of reference) is likely to correspond to the intraoperatively selected spinal level. As described in detail below, the method may employ the determination of an inter-level registration transform between the segmented surface data of the pre-selected spinal level and the adjacent segmented surface data of the adjacent spinal level in order to assist in the registration between the adjacent segmented surface data and the intraoperative surface data, thereby potentially improving the efficiency and accuracy of the quality measures that are determined.

Referring now to FIG. 1, an example system for performing intraoperative spine level verification is shown. The system includes a surface detection system 10 that is operably interfaced with control and processing hardware 100. The surface detection system 10 may be any suitable system for detecting, measuring, imaging, or otherwise determining the surface topography of one or more objects (such as, but not limited to, a region of an exposed spine of a patient 50) using optical radiation or sound waves (e.g. ultrasound). Non-limiting examples of suitable optical devices include laser range finders, photogrammetry systems, and structured light imaging systems, which project surface topography detection light onto a region of interest, and detect surface topography light that is scattered or reflected from the region of interest. The detected optical signals can be used to generate surface topography datasets consisting of point clouds or meshes. Other examples using sound waves for determining surface topography can include ultrasonography.

The example system may also include a tracking system 20, which may be employed to track the position and orientation of one or more medical instruments 40. The medical instrument 40 is shown having fiducial markers 45 attached thereto, and passive or active signals emitted from the fiducial markers 45 are detected by the tracking system 20 (e.g. a stereoscopic tracking system employing two tracking cameras). In an alternative example embodiment, the position and orientation of a medical instrument may be tracked via a surface detection subsystem 10, such as a structured light detection system, that is employed to detect the surface profile of a of at least a portion of the medical instrument, or structure attached thereto, and to determine the position and orientation of the medical instrument via comparison of the detected surface profile with a known surface profile.

Although not shown in FIG. 1, a tracked reference frame (e.g. a clamp with fiducial markers provided thereon or attached thereto) may be attached to the patient and may be tracked by the tracking system 20. Such a tracked reference frame may be employed for image-guided surgeries.

FIG. 1 also illustrates an example implementation of control and processing hardware 100, which includes one or more processors 110 (for example, a CPU/microprocessor), bus 105, memory 115, which may include random access memory (RAM) and/or read only memory (ROM), a data acquisition interface 120, a display 125, external storage 130, one more communications interfaces 135, a power supply 140, and one or more input/output devices and/or interfaces 145 (e.g. a speaker, a user input device, such as a keyboard, a keypad, a mouse, a position tracked stylus, a position tracked probe, a foot switch, and/or a microphone for capturing speech commands).

It is to be understood that the example system shown in FIG. 1 is illustrative of a non-limiting example embodiment, and is not intended to be limited to the components shown. Furthermore, one or more components of control and processing hardware 100 may be provided as an external component that is interfaced to a processing device. For example, as shown in the figure, one or both of the surface detection system 10 and the tracking system 20 may be included as a component of control and processing hardware 100 (as shown within the dashed line 101), or may be provided as one or more external devices.

Although only one of each component is illustrated in FIG. 1, any number of each component can be included in the control and processing hardware 100. For example, a computer typically contains a number of different data storage media. Furthermore, although bus 105 is depicted as a single connection between all of the components, it will be appreciated that the bus 105 may represent one or more circuits, devices or communication channels which link two or more of the components. For example, in personal computers, bus 105 often includes or is a motherboard. Control and processing hardware 100 may include many more or less components than those shown.

Control and processing hardware 100 may be implemented as one or more physical devices that are coupled to processor 110 through one of more communications channels or interfaces. For example, control and processing hardware 100 can be implemented using application specific integrated circuits (ASICs). Alternatively, control and processing hardware 100 can be implemented as a combination of hardware and software, where the software is loaded into the processor from the memory or over a network connection.

Some aspects of the present disclosure can be embodied, at least in part, in software. That is, the techniques can be carried out in a computer system or other data processing system in response to its processor, such as a microprocessor, executing sequences of instructions contained in a memory, such as ROM, volatile RAM, non-volatile memory, cache, magnetic and optical disks, or a remote storage device. Further, the instructions can be downloaded into a computing device over a data network in a form of compiled and linked version. Alternatively, the logic to perform the processes as discussed above could be implemented in additional computer and/or machine readable media, such as discrete hardware components as large-scale integrated circuits (LSI's), application-specific integrated circuits (ASIC's), or firmware such as electrically erasable programmable read-only memory (EEPROM's) and field-programmable gate arrays (FPGAs).

A computer readable medium can be used to store software and data which when executed by a data processing system causes the system to perform various methods. The executable software and data can be stored in various places including for example ROM, volatile RAM, non-volatile memory and/or cache. Portions of this software and/or data can be stored in any one of these storage devices. In general, a machine readable medium includes any mechanism that provides (i.e., stores and/or transmits) information in a form accessible by a machine (e.g., a computer, network device, personal digital assistant, manufacturing tool, any device with a set of one or more processors, etc.).

Examples of computer-readable media include but are not limited to recordable and non-recordable type media such as volatile and non-volatile memory devices, read only memory (ROM), random access memory (RAM), flash memory devices, floppy and other removable disks, magnetic disk storage media, optical storage media (e.g., compact discs (CDs), digital versatile disks (DVDs), etc.), among others. The instructions can be embodied in digital and analog communication links for electrical, optical, acoustical or other forms of propagated signals, such as carrier waves, infrared signals, digital signals, and the like. As used herein, the phrases "computer readable material" and "computer readable storage medium" refer to all computer-readable media, except for a transitory propagating signal per se.

Embodiments of the present disclosure can be implemented via processor 110 and/or memory 115. For example, the functionalities described below can be partially implemented via hardware logic in processor 110 and partially using the instructions stored in memory 115. Some embodiments are implemented using processor 110 without additional instructions stored in memory 115. Some embodiments are implemented using the instructions stored in memory 115 for execution by one or more microprocessors, which may be general purpose processors or specialty purpose processors. Thus, the disclosure is not limited to a specific configuration of hardware and/or software.

The control and processing hardware 100 is programmed with subroutines, applications or modules 150, which include executable instructions, which when executed by the one or more processors 110, causes the system to perform one or more methods described in the present disclosure. Such instructions may be stored, for example, in memory 115 and/or other internal storage. In particular, in the example embodiment shown, registration module 155 includes executable instructions for registering segmented surface data (obtained from the volumetric image data 30) with intraoperative surface data that is obtained using the surface detection system 10. The registration module 155 may also be employed for computing registration quality measures associated with the quality of registration between the segmented surface data and the intraoperative surface data, thereby generating measures for verifying the identification of the intraoperative spinal level. The navigation user interface module 160 includes executable instructions for displaying a user interface for performing, for example, image-guided surgical procedures.

Figure 5A:
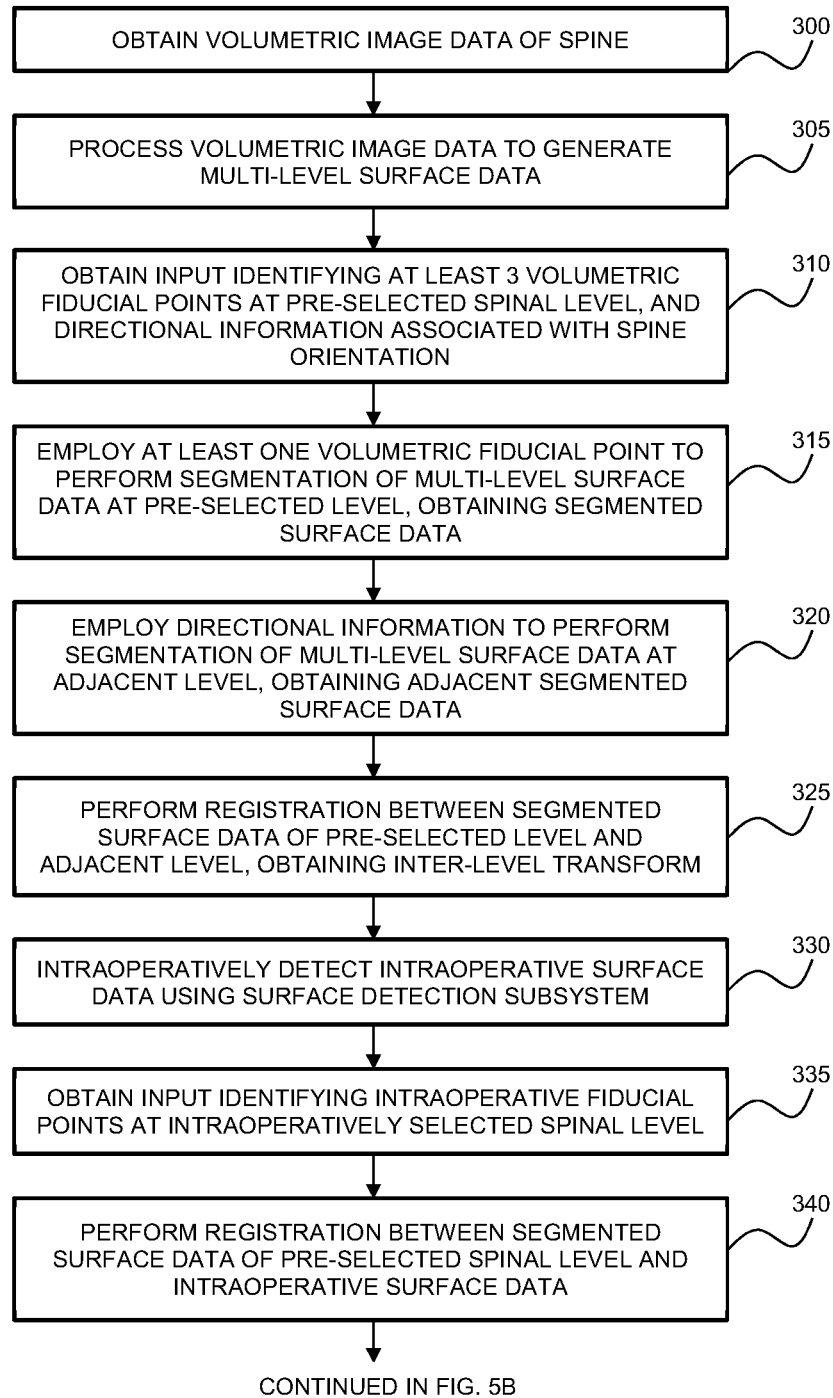
FIGS. 5A-B provide a flow chart illustrating an example method of intraoperative spinal verification.
Figure 5B:
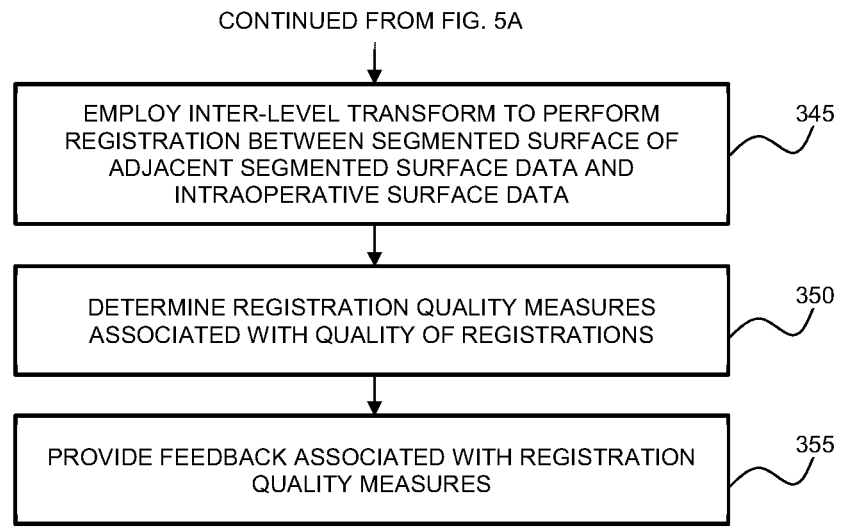

Referring now to FIGS. 5A and 5B, an example method is henceforth described for providing verification of the correspondence of an intraoperatively exposed spinal level with a spinal level pre-selected based in volumetric image data. It will be understood that some of the steps illustrated in the flow chart shown in FIGS. 5A and 5B need not be performed in the order shown. Various example embodiments of the present disclosure that pertain to spinal level verification employ the registration of segmented surface data (obtained by processing volumetric image data of the spine) with intraoperative surface data (intraoperatively obtained using a surface detection system; also known as a surface topography detection system or surface profile detection system). The volumetric image data, obtained in step 300 of FIG. 5A, may be obtained preoperatively, using, for example, imaging modalities such as, but not limited to, computed tomography (CT) and magnetic resonance imaging (MRI). Alternatively, the volumetric image data may be obtained intraoperatively, for example, using intraoperative CT or intraoperative MRI.

As described above, in some example embodiments, spinal level verification during or after a spinal procedure involving an exposed portion of the spine may be achieved by performing registration between segmented surface data (obtained from volumetric image data) and intraoperative surface data, and comparing the quality of registration when the segmented surface data originates from different levels within the volumetric frame of reference. In one example embodiment, segmented surface data is obtained from the volumetric image data, such that the segmented surface data corresponds to a pre-selected spinal segment that is expected to be exposed or identified during the surgical procedure. The segmented surface data from the pre-selected spinal level, and adjacent segmented surface data from an adjacent spinal level that is adjacent to the pre-selected spinal level, is registered to the intraoperative surface data, and quality measures associated with the registration are obtained, thereby permitting an assessment or a determination of whether or not the pre-selected spinal surface (in the volumetric frame of reference) is likely to correspond to the intraoperatively selected spinal level.

Figure 2A:
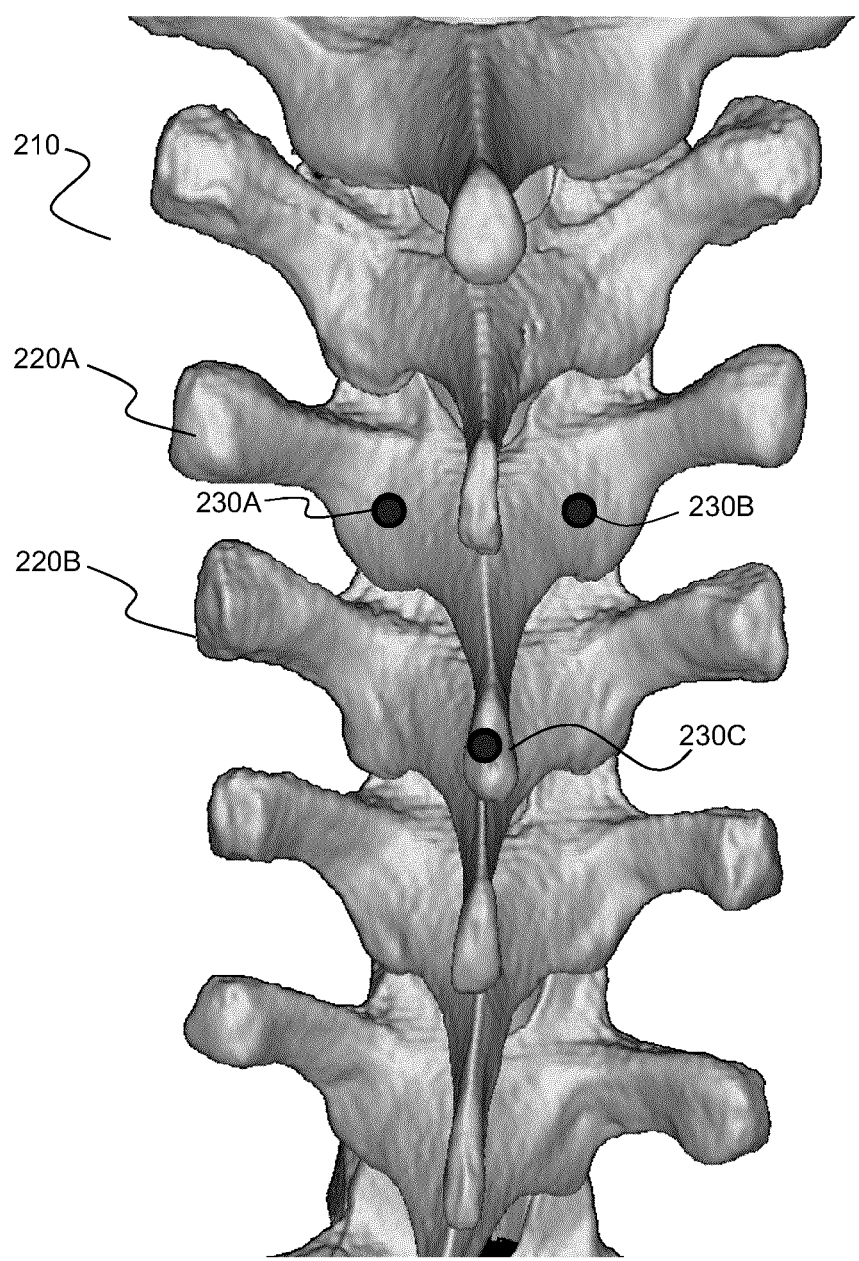
FIG. 2A illustrates an example multi-level surface generated by thresholding volumetric image data of the spine to determine a surface corresponding to bone, showing the pre-selected spinal level that is expected to correspond to a selected intraoperatively exposed spinal level. The figure also shows three volumetric fiducial points located at the pre-selected spinal level.

When performing the aforementioned example method, the pre-selected spinal level, within the volumetric frame of reference, may be identified by the selection, by a user (such as, but not limited to, a surgeon performing the surgical procedure), of a set of at least three fiducial points in the volumetric frame of reference. These fiducial points are henceforth referred to as volumetric fiducial points. The volumetric fiducial points may be selected by processing the volumetric image data to generate a multi-level surface data characterizing the surface of the spine, as shown at step 305 of FIG. 5A. An example a multi-level surface 210 is shown in FIG. 2A. In the multi-level surface image 210 of the spine, many volumetric spinal levels can be seen, allowing determination of the identity (i.e. level number) of a given volumetric spinal level. This multi-level surface 210, characterized by associated multi-level surface data, resides in the volumetric frame of reference that is associated with the volumetric image data.

The multi-level surface data may be generated according to a wide variety of methods. One example is by selecting a bone threshold and generating an isosurface using the marching cubes algorithm from the volumetric image data. Another example is to construct an isocontour from each 2D slice of a volumetric image data based on a bone threshold, and stitching the slices together into a 3D surface.

As noted above, the multi-level surface 210 may be employed for the selection of a set of at least three volumetric fiducial points, shown at 230A-C, as per step 310 of FIG. 5A. The volumetric fiducial points 230A-C, which may be selected by an operator on a user interface displaying the multi-level surface data 210, identify the pre-selected spinal level 220 that is expected to be exposed during a surgical procedure.

Figure 2B:
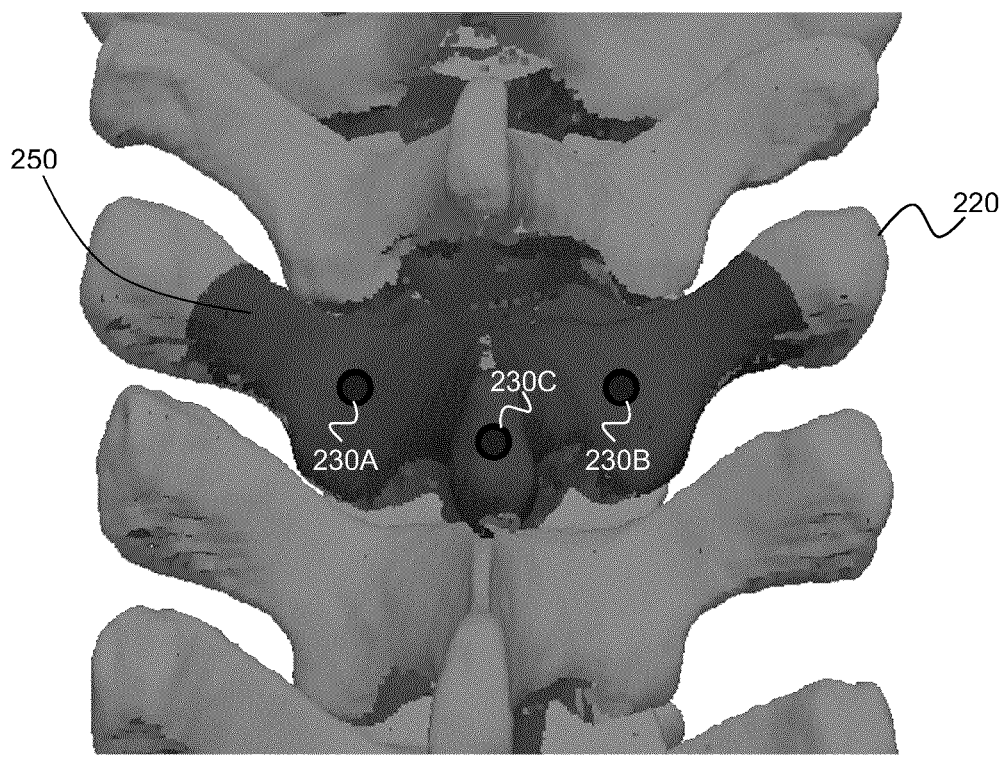
FIG. 2B illustrates an example segmented surface, obtained by segmenting the multi-level surface of FIG. 2A at the pre-selected spinal level (as identified by the volumetric fiducial points).

Having identified the volumetric fiducial points 230A-C, the multi-level surface data 210 may be processed to generate the segmented surface data associated with the pre-selected level 220A. An example of the segmented surface data 250 is shown in FIG. 2B, which also shows the volumetric fiducial points 230A-C. The segmented surface data 250 includes surface data corresponding to the pre-selected level 220A. Segmentation of the multi-level surface data to obtain the segmented surface data may be performed according to any suitable method. One or more of the volumetric fiducial points may be employed to initiate surface segmentation, as shown at step 315 of FIG. 5A.

Non-limiting examples of surface segmentation methods include non-template-based methods and methods which utilize anatomical shape models. Non-template-based methods can utilize geometrical properties, such as connectivity, surface normals, and curvatures to determine the boundary of the segmented region, or statistical properties, such as variance from nearby neighboring points on the surface. Methods based on anatomical shape models can utilize a pre-computed atlas of vertebra as a template to perform the segmentation. Both classes of method can also be used in combination. In all these methods, one or more volumetric fiducial points can serve as a seed point to initialize the segmentation process. Alternatively, for segmentation methods which are fully automatic and operate on the entire volumetric data (which are usually based on anatomical atlases), one or more volumetric fiducials can be used to tag the level(s) of interest.

Figure 2C:
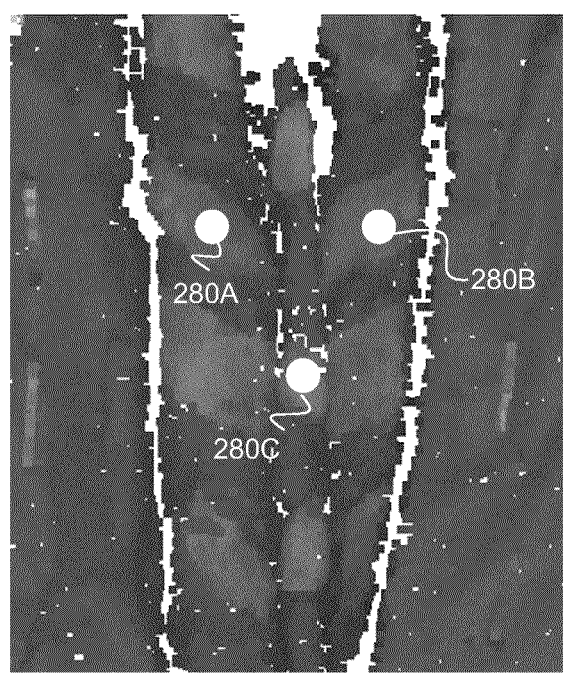
FIG. 2C illustrates an intraoperative surface detected using a surface detection system, showing several intraoperatively exposed spinal levels. Three intraoperative fiducial points, corresponding to the volumetric fiducial points, identify the intraoperatively selected spinal segment that is believed to correspond to the pre-selected spinal level in the volumetric frame of reference.
Figure 2D:
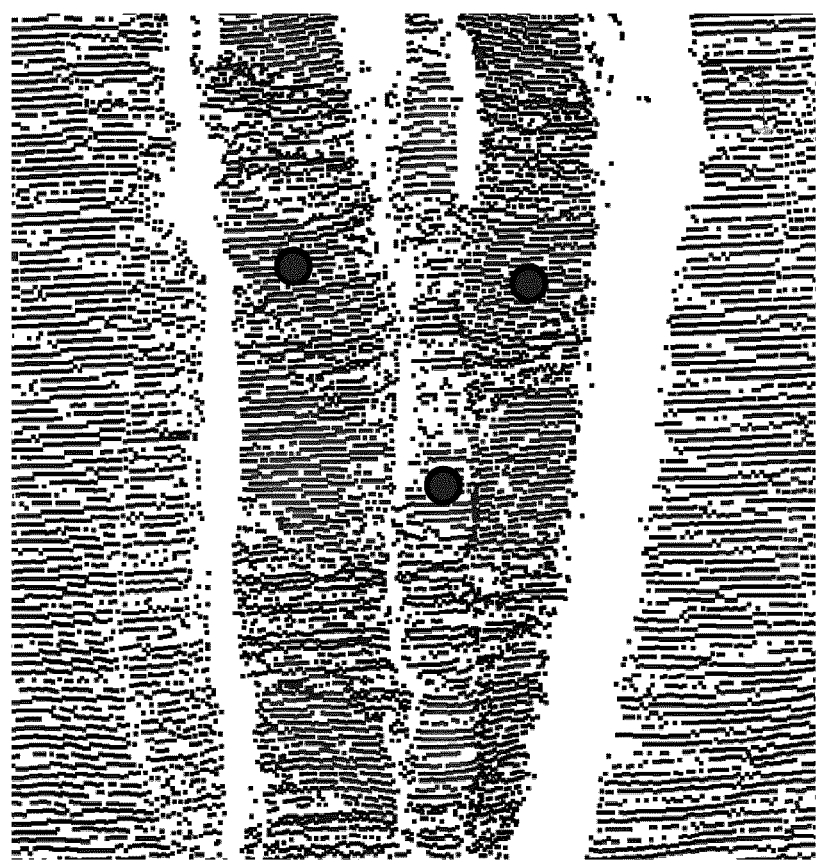
FIG. 2D provides a detailed view of the intraoperative surface shown in FIG. 2C.

Having generated the segmented surface data corresponding to the pre-selected spinal level in the volumetric frame of reference, the segmented surface data may be registered to the intraoperative surface data of the exposed spine, detected using a surface detection system, as shown in step 330 of FIG. 5A, where the registration step is shown in step 340. As noted above, the intraoperative surface data may be obtained using a surface detection system such as, but not limited to, a structured light detection system. FIG. 2C shows an example of intraoperative surface data detected using a structured light detection system. A zoomed in view is provided in FIG. 2D. In contrast to the multi-level surface data 210 shown in FIG. 2A, the intraoperative surface data only has partial bone exposed, and may contain multiple spinal levels in the field of view.

Input is also received that is indicative of the locations of intraoperative fiducial points 280A-C (shown in FIG. 2C), in the intraoperative frame of reference, where each intraoperative fiducial point corresponds to a respective volumetric fiducial point, as shown at step 335 of FIG. 5A. The intraoperative fiducial points 280A-C thus identify an intraoperatively selected spinal level that is expected to correspond to (i.e. have the same spinal level as) the pre-selected spinal level. The input can be received, for example, via the use of a tracked probe, such as the tracked probe 40 shown in FIG. 1, where the tracked probe is positioned with its tip at a desired intraoperative fiducial point, and input is provided by the user indicating that the location of the tracked probe corresponds to a given volumetric fiducial point.

According to the present example embodiment, adjacent segmented surface data is also generated for an adjacent spinal level that is adjacent to the pre-selected spinal level. An example of an adjacent level is shown in FIG. 2A at 220B. Unlike the pre-selected spinal level 220A, the adjacent spinal level 220B does not have associated volumetric fiducial points to support surface segmentation from the multi-level surface data, or to support registration with the intraoperative surface data.

In order facilitate surface segmentation of the adjacent spinal level, an adjacent volumetric region, such as a bounding box (the region need not be a rectangular prism) is identified in which to perform segmentation. The determination of the adjacent volumetric region may be made based on a determination of directional information associated with the orientation of the spine, where the directional information enables the determination of a direction in which to locate the adjacent spinal level. The directional information can be a direction which defines the entire spine. Alternatively, the directional information can be described by a spline or a piece-wise linear function to follow the shape of the spine.

This directional information may be obtained according to a variety of methods, non-limiting examples of which are provided below. In one example implementation, the directional information may be obtained from information associated with the volumetric image data, such a superior-inferior direction provided from the DICOM header. In another example implementation, an axis associate with the orientation of the spine may be determined from principal component analysis. In another example implementation, image processing methods may be applied to the volumetric image data to extract an estimated shape of the spine.

In one example implementation, a set of local spine axes may be determined, thereby providing directional information on a per-level basis. A preferential axis is initially determined for segmenting the volumetric image data. The preferential axis may be determined, for example, from information associated with the volumetric image data, such a superior-inferior direction provided from a DICOM header, or from principle component analysis. The preferential axis may then be employed to segment the volumetric image data into a series of volumetric slabs that are arranged along the preferential axis, each of which are analyzed to locate the spine. The choice of slab thickness depends on the resolution required for computing the directional information of the spine. On the other hand, if the slab thickness is too thin, the accuracy of finding the spine within the slab, and hence deriving the directional information, may be degraded, due to reduction of signal (e.g. structures that belong to the spine) to noise (e.g. the background). A slab thickness of approximately half of the length of a spinal level is typically suitable.

Various methods can be employed to analyze the slabs in order to derive the directional information of the spine. One example method can be template-based, wherein the slabs are compared to a pre-computed atlas of different vertebra. Alternatively, a user-defined threshold can be used to define a contour and/or isosurface of the bone, from which the vertebra region within the slab can be identified. The vertebra region can be identified by performing an iterative search for structures that resemble the vertebra according to a pre-computed atlas. Alternatively, an atlas-free method can be employed, which utilizes one or more volumetric fiducial points as a starting point via an iterative search.

For the atlas-free method, an initial volumetric slab segment containing one or more of the volumetric fiducial points is identified. An initial bounding box (or other suitable confining volumetric region) is then determined, where the initial bounding box contains, and is centered on, or approximately centered on, one or more of the fiducial points. The size of the initial bounding box may be determined, for example, based on the spatial extent of the segmented surface data associated with the pre-selected level, or based on an estimated spatial extent of an average spinal level. This initial volumetric slab segment is processed, within the initial bounding box, to determine an initial center of mass of bony structures within the initial volumetric slab segment. This process may be repeated one or more times, where each time, the bounding box is re-centered on the most recently identified center of mass location. The center of mass location may be iteratively refined in this manner until a pre-selected convergence criterion has been met.

Once the center of mass corresponding to the spine has been determined in the initial volumetric slab, an adjacent bounding box may then be determined, within an adjacent slab. Since the size of an adjacent vertebra is approximately the same within the same patient, the adjacent bounding box can be of the same size as the bounding box from the initial volumetric slab, wherein the center of the adjacent bounding box can be initialized with the center of mass from the initial volumetric slab. This adjacent volumetric slab segment is processed similarly, within the adjacent bounding box, to determine an adjacent center of mass location within the adjacent volumetric slab segment. As noted above, this process may be repeated one or more times, where each time, the bounding box is re-centered on the most recently identified center of mass location, iteratively refining the center of mass location until a pre-selected convergence criterion has been met.

The above method of finding an adjacent center of mass location in an adjacent volumetric slab segment may then be repeated one or more times in order to determine center of mass locations within a plurality of the volumetric slab segments, thereby allowing the determination of a local axis, based on two or more center of mass locations. In one example implementation, the local axis associated with two neighbouring volumetric slab segments may be employed to locate the bounding box within an adjacent volumetric slab region when performing the aforementioned method.

In situations where the initial preferential axis is significantly different than the directional information of the spine (e.g. due to disease), the computed directional information can be used to again segment the volumetric image data into a series of volumetric slabs, and the above iterative center finding method repeated to refine the directional information of the spine.

After obtaining the directional information (e.g. global or local), this information may be employed to determine an adjacent volumetric region within which to perform segmentation of the multi-level surface data in order to obtain the adjacent segmented surface data corresponding to the adjacent spinal level, as shown at step 320 of FIG. 5A. For example, an adjacent bounding box for segmenting the adjacent spinal level may be centered at a location, relative to one or more of the volumetric fiducial points, which lies along an axis obtained based on the directional information, such that the bounding box is expected to contain the adjacent spinal level. The spatial separation between the center of the adjacent bounding box and the one or more volumetric fiducial points may be determined, for example, based on the spatial extent of the segmented surface data associated with the pre-selected spinal level, or based on reference anatomical data (e.g. atlas data) characterizing an estimated spatial separation between the pre-selected spinal level and the adjacent spinal level.

The multi-level surface data may be processed within the adjacent bounding box to generate the segmented surface data associated with the adjacent spinal level. As noted above, the segmentation of the multi-level surface data to obtain the adjacent segmented surface data may be performed according to any suitable method.

Having generated the segmented surface data from the volumetric image data, for both the pre-selected spinal level and an adjacent level that is adjacent to the pre-selected level, registration may be performed between the intraoperative surface data and each of (i) the segmented surface data corresponding to the pre-selected spinal level, and (ii) the adjacent surface data corresponding to the adjacent spinal level, as shown at step 340 of FIG. 5A and step 345 of FIG. 5B.

When registering the segmented surface data (corresponding to the pre-selected spinal level) to the intraoperative surface data, the identified volumetric fiducial and respective intraoperative fiducial points may be employed to perform an initial registration (based on the correspondence of the volumetric and intraoperative fiducial points). A suitable surface-to-surface registration method (algorithm) may then be employed to perform registration between the segmented surface data and the intraoperative surface data.

It will be understood that any suitable surface registration method may be employed to perform registration between surfaces, when performing methods according to the example embodiments disclosed herein. Non-limiting examples of suitable registration methods include the iterative closest point algorithm, wherein the distance between points from difference surfaces are minimized.

Registration is also performed between the adjacent segmented surface data and the intraoperative surface data, as shown at step 325. However, unlike the case of the segmented surface data corresponding to the pre-selected spinal level, volumetric fiducial locations may not be known for the adjacent segmented surface data. An approximation of an initial registration of the adjacent segmented surface data to the intraoperative surface data can be determined from the result of the registration between the segmented surface data and the intraoperative surface data, and then applying a translation according to the previously computed directional information of the spine. However, this method may be inaccurate.

This can be addressed by determining an inter-level transform between the pre-selected spinal level and the adjacent spinal level, also as shown at step 325. As described below, once such a transform is known, the transform can be used as the initial registration of the adjacent segmented surface data to the intraoperative surface data, and then refined by any suitable surface registration algorithm. In addition, the volumetric fiducial points associated with the pre-selected spinal level may be transformed and applied to the adjacent spinal level, thus facilitating segmentation and registration between the adjacent segmented surface data and the intraoperative surface data.

The inter-level transform between the pre-selected spinal level and the adjacent spinal level may be determined by performing registration between the segmented surface data (associated with the pre-selected spinal level) and the adjacent segmented surface data. The initial transform relating the segmented surface data and the adjacent surface data is defined by following the pre-computed directional information, translating by a distance that is based on the spatial extent of the segmented surface data, or using reference anatomical data (e.g. atlas data) characterizing an estimated spatial separation between the pre-selected spinal level and the adjacent spinal level. Fine-tuning of the registration is then performed by any suitable registration algorithm.

Having obtained the inter-level transform between segmented surface data and the adjacent segmented surface data, the location and orientation of the adjacent spinal level, relative to that of the pre-selected spinal level, is known, and this information can be used to guide registration between the adjacent segmented surface data and the intraoperative surface data.

Figure 3A:
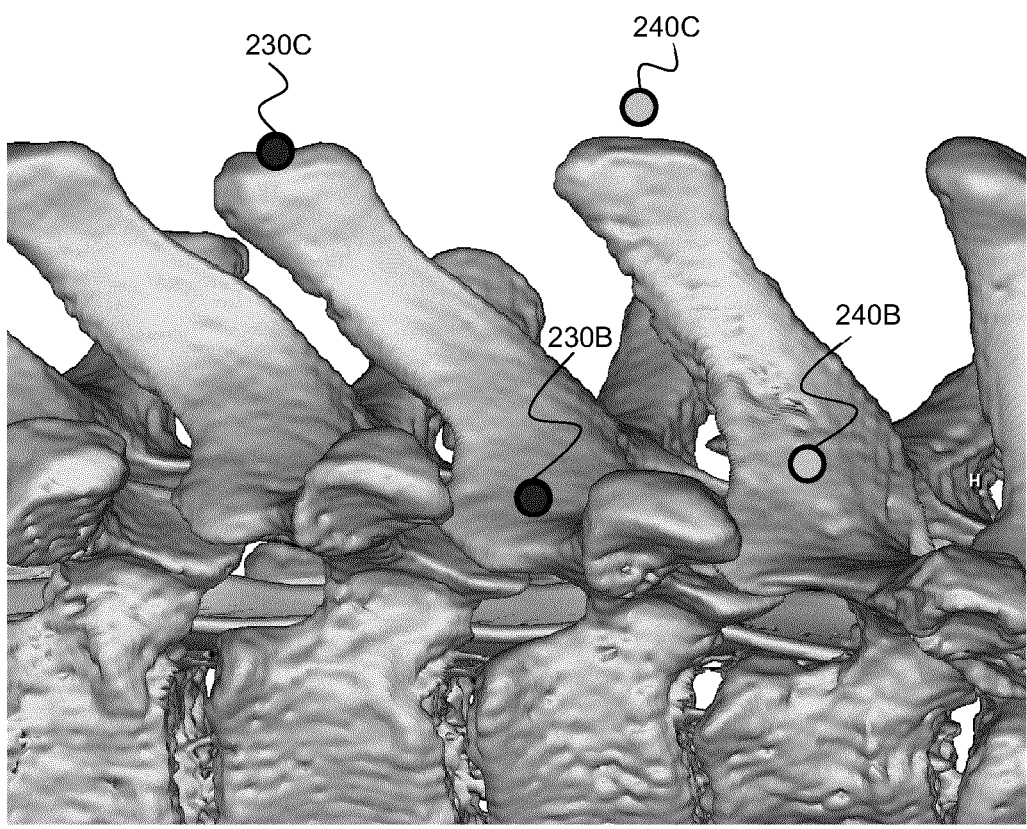
FIG. 3A illustrates the process of shifting the volumetric fiducial points via the inter-level transform, in order to generate adjacent volumetric fiducial points at an adjacent spinal location.

In one example implementation, the inter-level transform may be employed to determine locations, in the adjacent segmented surface data, of adjacent volumetric fiducial points that correspond to the volumetric fiducial points of the pre-selected spinal level. According to this example implementation, and as illustrated in FIG. 3A, the inter-level transform may be applied to the locations of the volumetric fiducial points 230A-C associated with the pre-selected fiducial points in the volumetric frame of reference, such that the volumetric fiducial points 230A-C are transformed to the region associated with the adjacent spinal level (FIG. 3A shows volumetric fiducial points 230B and 230C, as volumetric fiducial point 230A is hidden in the view shown).

Figure 3B:
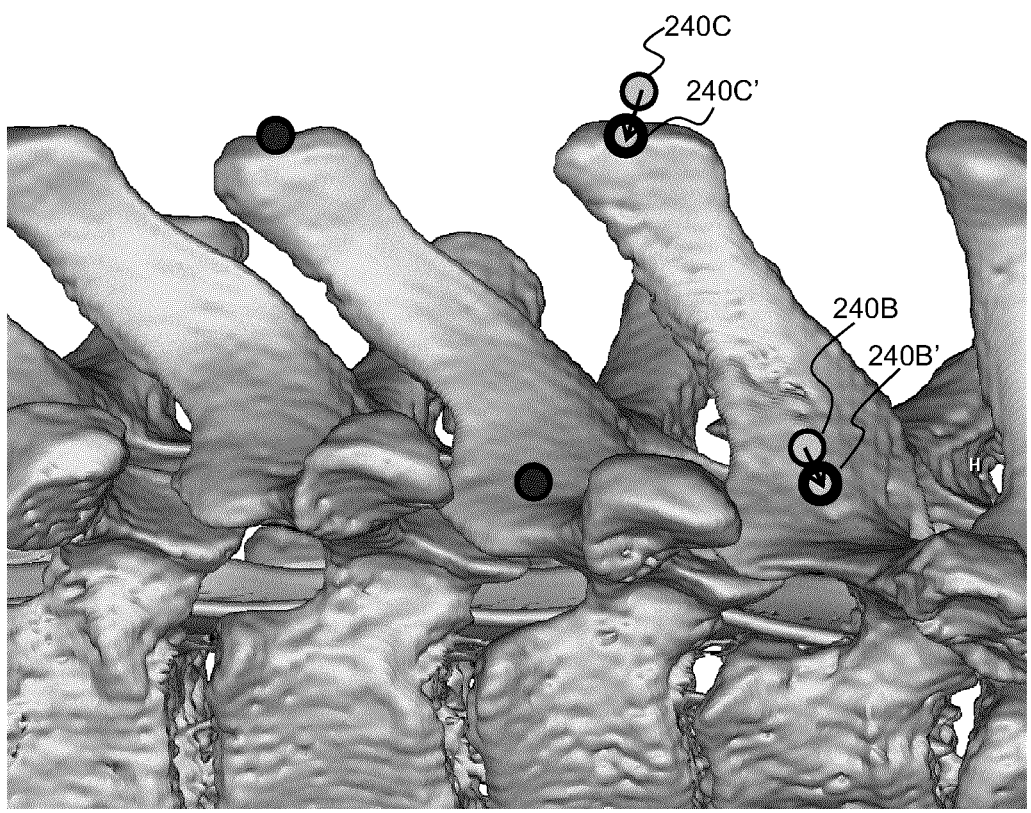
FIG. 3B demonstrates an example method of "snapping" the shifted volumetric fiducial points onto the adjacent segmented surface.

Since the segmented surface data that is associated with the pre-selected surface is different than the adjacent segmented surface data associated with the adjacent level, the transformed volumetric fiducial points 240B-C may not lie within the adjacent surface data. This effect is illustrated in FIG. 3B, where, for example, transformed points 240B and 240C initially lie above the adjacent segmented surface. In order to bring the transformed points 240B-C into the adjacent segmented surface data, the transformed points 240B-C may be shifted so that they lie within the adjacent segmented surface, as shown at points 240B' and 240C' in FIG. 36.

For example, this may be achieved by computing a location within the adjacent segmented surface data that is nearest to the transformed point, and shifting ("snapping") the transformed point to this nearest location, thereby obtaining the adjacent volumetric fiducial point that lies within the adjacent segmented surface data. Alternatively, the point shifting procedure may be performed by computing the local surface normal vector that is directed at the transformed fiducial point, and shifting the transformed fiducial point along the direction corresponding to this vector. Optionally, in combination with these methods of shifting the fiducials, multiple candidate nearest locations on the adjacent segmented surface may be evaluated, wherein the choice is made based on a similarity measure of each candidate to the fiducial on the segmented data. This similarity measure can be based on surface normals and curvatures in addition to proximity.

Having generated the adjacent volumetric points within the adjacent surface data corresponding to the adjacent surface level, the adjacent segmented surface data can be registered to the intraoperative surface data, as shown at step 345 of FIG. 5B, using the adjacent volumetric fiducial points and the intraoperative volumetric fiducial points to perform the initial registration, followed by surface-to-surface registration using a suitable registration method.

To refine the registration further, the adjacent volumetric points can be used to segment the adjacent surface data, producing an adjacent segmented surface data that is segmented similar to the pre-selected spinal level, which can be used for registration.

In an alternative example implementation, the registration of the adjacent segmented surface data to the intraoperative surface data may be achieved using the inter-level transform, but without generating the adjacent volumetric fiducial points. For example, the combination of the inter-level transform (between the adjacent segmented surface data and the segmented surface data) and the registration transform (resulting from the registration of the segmented surface data to the intraoperative surface data) may be employed to generate an initial registration of the adjacent segmented surface to the intraoperative surface data, and a suitable surface-to-surface registration algorithm may then be employed to complete the registration.

After performing the registration between the intraoperative surface data and each of (i) the segmented surface data corresponding to the pre-selected spinal level, and (ii) the adjacent segmented surface data corresponding to the adjacent spinal level, registration quality measures may be calculated that characterize the quality of the respective registrations, as shown at step 350 of FIG. 5B.

One example measure of registration quality is the registration error, which describes the mean distance between points of the segmented surface data to the registered intraoperative surface data. Another example measure of registration quality is the standard deviation of the distances between points of the segmented surface data to the registered intraoperative surface data. An additional example of measure of registration quality is the number of points that are matched between the surface data. Yet another example, is how the points from the intraoperative surface data are spatially distributed on the segmented surface data after registration, such as the ratio of the number of points to the surface area of the segmented surface data. These metrics, or other suitable registration quality measures, can be used alone or in combination. One example method to combine these metrics is to evaluate the ratio of the different metrics. If two metrics disagree, the choice for a more desired registration quality can be based on the one metric whose relative difference is greatest. Another example to combine the use of different metrics is to train a computational model by presenting it with examples of registrations at correct and incorrect spinal levels. Examples of such models can include a logistic regression classifier, a random forest, a support vector machine, or a neural network, which can be used to calculate a registration quality measure.

The registration quality measures may be employed to provide feedback for evaluating and verifying the validity of the identity of the intraoperatively selected spinal level relative to the pre-selected spinal level, as shown at step 355 of FIG. 5B. Therefore, in some example embodiments, feedback associated with the registration quality measures may be provided, where the feedback is suitable for inferring whether or not the intraoperatively selected spinal level is likely to correspond to the pre-selected spinal level. This feedback can take a wide variety of different forms, such as providing the registration quality measures, or one or more other measures derived from the registration quality measures. For example, in the case that the registration quality measure associated with the registration between the segmented surface data and the intraoperative surface data is not the highest registration quality measure, the feedback may indicate that the intraoperatively selected spinal level may not correspond to the pre-selected spinal level.

Figure 4B:
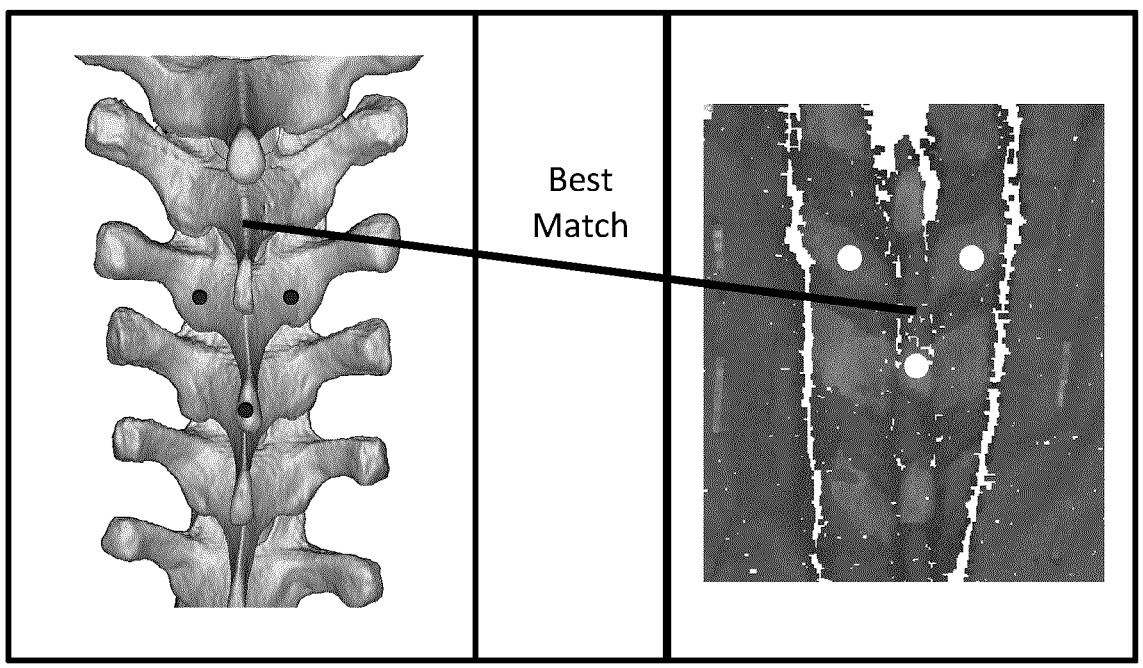
Figure 4C:
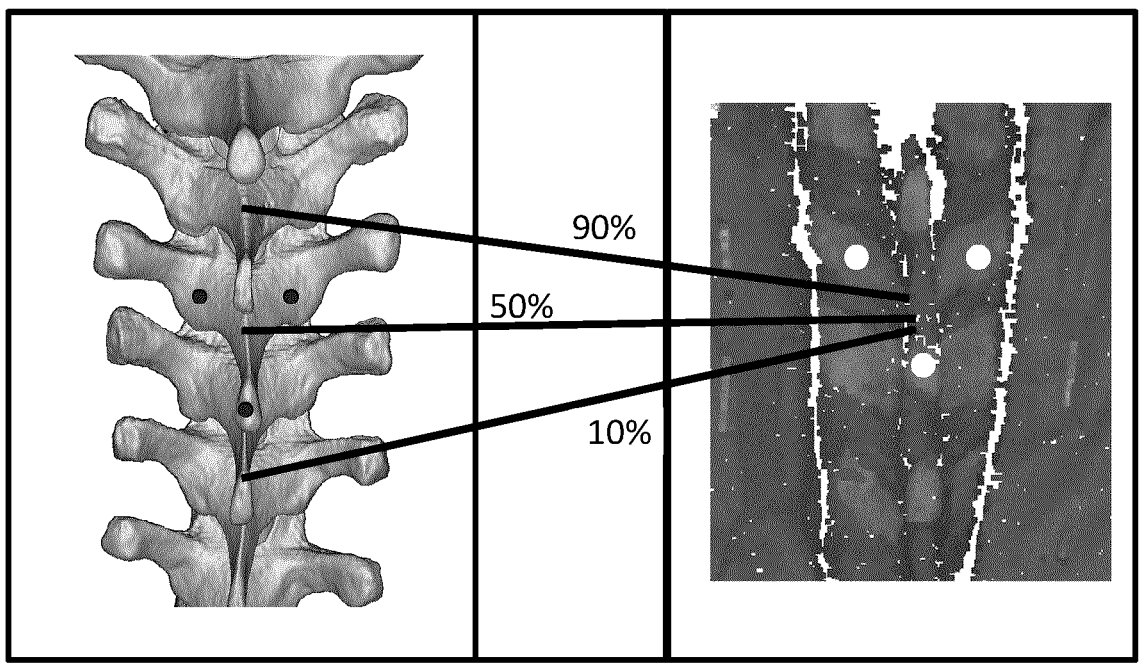

In one example implementation, the feedback can include a display of the registration quality measures for the registration between the intraoperatively selected level and each of (i) the pre-selected spinal level, and (ii) the adjacent spinal level. For example, as shown in FIG. 4A, the feedback can be text-based, wherein the user is notified that the intraoperative fiducials may be incorrect, and a suggestion and option is made available to re-do registration. Alternatively, a more graphical presentation may be used. As shown in FIG. 4B, a single suggestion is provided to the user to indicate which spinal level resulted in the highest registration quality. Alternatively, as shown in FIG. 4C, the system can show a metric for each volumetric spinal level that has been registered to the intraoperative surface data.

In one example implementation, the feedback can include estimates of the probability of the intraoperatively selected level being identified as the pre-selected spinal level, and optionally the adjacent spinal level, based on the registration quality measures. One such probability estimate can be derived based on the distribution of distances between points of the segmented surface data to the registered intraoperative surface data. The distributions corresponding to two registrations can be compared by any suitable statistical tests. If the distributions can be approximated by a normal distribution, a Z-test may be used. Alternatively, nonparametric tests such as the Kolmogorov-Smirnov test can be employed.

In one example implementation, the feedback can include a determination of the estimated identity of the intraoperatively selected level, based on the registration quality measures, if the identity of the levels in the volumetric image data are known (e.g. if input is provided by the user identifying at least one level in the surface segmented from the volumetric image data and the superior-inferior direction is known).

In one embodiment, the registration between the segmented surface data (or the adjacent segmented surface data) and the intraoperative surface data may be achieved without segmentation (or cropping) of the intraoperative surface data, even though the intraoperative surface data may include surface topography extending beyond the intraoperatively selected level, where the additional surface topography may include regions such as adjacent spinal levels. In one example implementation, these regions may be retained because the segmented surface data (or the adjacent segmented surface data) is first initially registered to the intraoperative surface data corresponding to the intraoperatively selected spinal level, and contains only regions belonging to one spinal level. Additional intraoperative surface data outside of the intraoperative selected spinal level cannot also be registered to the segmented surface data. In other words, provided that the segmented surface data (or the adjacent segmented surface data) is initially spatially aligned to the intraoperatively selected spinal level, and only spatially extends within the spatial region corresponding to this level, the presence of additional spinal levels will not affect the registration quality.

However, it will be understood that in some example embodiments, the intraoperative surface data may be segmented to a spatial region pertaining to the intraoperatively selected level, prior to performing registration. In one example implementation, this segmentation may be achieved, for example, based on an expected spatial extend relative to one or more of the intraoperative fiducial points. The expected spatial extent may be determined, for example, based on atlas data, or, for example, based on the spatial extent of the segmented surface data corresponding to the pre-selected spinal level in the volumetric frame of reference.

It will be understood that the aforementioned example embodiment may be adapted to also include the determination of one or more registration quality measures based on the processing of second adjacent segmented surface data corresponding to a second adjacent spinal level that also lies adjacent to the pre-selected spinal level, but on the opposite side of the pre-selected spinal level compared to the aforementioned first adjacent spinal segment. Such an example embodiment permits the verification of the identity of the intraoperatively selected spinal level relative to: (i) the pre-selected spinal level, (ii) the first adjacent spinal level residing on one side of the pre-selected spinal level, and (iii) the second adjacent spinal level residing on the opposite side of the pre-selected spinal level. Such a method therefore permits the verification of the identity of the intraoperatively selected spinal level with a tolerance of plus or minus one spinal level relative to the pre-selected spinal level. In such a case, the feedback pertaining to the three registration quality measures may provide an indication of the most likely correspondence between the intraoperatively selected spinal level and the three spinal levels from the volumetric frame of reference, for which the spinal level is known.

It is also possible to extend the previously described example embodiments such that the intraoperatively defined spinal level is compared, via registration, with one or more additional adjacent levels. For example, this comparison may be achieved by calculating registration quality measures associated with the registration of the intraoperative surface data with: (i) segmented surface data associated with the pre-selected spinal level, (ii) adjacent segmented surface data associated with one or more adjacent spinal levels on either side of the pre-selected spinal level, and additional adjacent segmented surface data that is associated with one or more additional adjacent spinal levels that are each separated from the pre-selected spinal level by two levels. The registration of the additional adjacent segmented surface data with the intraoperative surface data may be achieved by computing an additional inter-level transform, using the methods described above (e.g. translating the adjacent volumetric fiducial points to the additional adjacent surface data via the adjacent inter-level transform). The additional segmented surface data, corresponding to a given additional adjacent spinal level, may be determined, for example, by employing the adjacent segmented surface data and the directional information to determine an additional adjacent volumetric region within which to perform segmentation of the multi-level surface data. For example, a suitably-sized bounding box for segmenting the additional adjacent surface data may be determined based on the spatial extent of the adjacent segmented surface data, and this bounding box may be positioned, relative to the adjacent spinal level, based on the directional information (global or local).

In one example embodiment, additional registration quality measures may be obtained when the intraoperative surface data includes more than one spinal level. For example, the inter-level transform obtained in the volumetric frame of reference may be employed to perform segmentation of the intraoperative surface data within a region corresponding to an adjacent intraoperative spinal level. This may be achieved, for example, by employing the inter-level transform to position, relative to one or more intraoperative fiducial points, a bounding box for segmenting the intraoperative surface data in a region corresponding to the adjacent intraoperative spinal level. Although the inter-level transform may not be completely accurate due to changes in the intraoperative spine orientation relative to the spine orientation in the volumetric image data, the change on a single level (or, for example, two or three levels) should be sufficiently small to permit the use of the inter-level transform. The inter-level transform may also be employed to shift the intraoperative fiducial points, in order to generate adjacent intraoperative fiducial points corresponding to the adjacent intraoperative level. Alternatively, the additional registration quality measures, associated with one or more additional spinal levels, may be obtained by registration of the segmented surface data with the intraoperative surface data, where an initial registration is obtained based on additional intraoperative fiducials that are provided for each additional spinal level. For example, a user may provide input identifying intraoperative fiducial points for the spinal levels adjacent to the intraoperatively selected spinal level, and additional registration quality measures may be obtained for these additional spinal levels.

In some cases, when processing the registration quality measures to generate feedback, it may be determined that an adjacent spinal level (in the volumetric frame of reference) or an additional adjacent spinal level provides a better match with the intraoperatively selected spinal level (i.e. improved registration; a higher registration quality measure) relative to the segmented spinal level associated with the pre-selected spinal level. In such a case, the feedback may include an indication that an alternative intraoperative spinal level is expected to be a better match (correspond more closely) to the pre-selected spinal level. In such a case, the operator may provide input for identifying, in a region associated with the alternative intraoperative spinal level, alternative intraoperative fiducial points. The aforementioned methods may then be repeated for this alternative intraoperative spinal level, in order to generate registration quality measures associated with the quality of registration between the segmented alternative intraoperative surface data (corresponding to the alternative intraoperative level) and the segmented surface data (corresponding to the pre-selected spinal segment), and optionally to adjacent surface data (corresponding to an adjacent spinal segment), in order to confirm the identification of the alternative intraoperative spinal level. Alternatively, instead of relying on a user or operator to provide the alternative intraoperative fiducial points, the alternative intraoperative fiducial points may be automatically generated using the inter-level transform between the pre-selected spinal level and the spinal level corresponding to the highest quality measure.

Although the preceding example embodiments involve the verification, on a per-level basis, of a selected intraoperative spinal level based on registration between segmented surface data (obtained from volumetric image data) and intraoperative surface data, it will be understood that these embodiments may be readily adapted to involve verification, and registration, using multiple contiguous levels. For example, the verification methods disclosed above may employ, instead of a single level, two or more contiguous spinal levels (i.e. spinal levels that are in sequence; e.g. levels 2 and 3, or levels 4, 5 and 6). For example, in the aforementioned example verification embodiment involving the registration of segmented surface data with the intraoperative surface data and adjacent segmented surface data with the intraoperative surface data, the segmented surface data, the adjacent surface data, and the intraoperative surface data may correspond to two or more contiguous spinal levels. In such a case, the three or more volumetric fiducial points may span the set of contiguous spinal levels of the segmented surface data, and the intraoperative fiducial points may span the set of contiguous spinal levels of the intraoperative surface data.

Examples

The following examples are presented to enable those skilled in the art to understand and to practice embodiments of the present disclosure. They should not be considered as a limitation on the scope of the disclosure, but merely as being illustrative and representative thereof.

The following example description describes a non-limiting example scenario from which an example implementation of the aforementioned embodiments can be used in surgery of the spine for level identification. According to this example method, volumetric image data containing multiple levels of the spine from a patient is first acquired, for example, via CT. This data is imported into the system used for spinel level verification. The user of the system selects a threshold, which is used to generate a multi-level surface of the bone using the marching cubes algorithm.

The user then selects at least three fiducials, for example, one on the left lamina, one on the spinous process, and one of the right lamina, via a user interface to specify the level of the spine which is the desired level to verify intraoperatively. These three volumetric fiducials are stored in the system's memory.

The system determines the direction of the spine by using the center of mass of the selected volumetric fiducials as a seed point to iteratively find the center of mass of the spine from the multi-level surface of the bone. The computed directional information of the spine is stored in the system's memory.

The three volumetric fiducials are used to perform region growing of the pre-selected spinal level on the multi-level surface data. Each fiducial is used as a seed point, and then region growing is performed by analyzing the neighboring points, and terminating the growth when it detects a spatial discontinuity. This segmented surface data is stored in the system's memory.

A rectangular bounding box is generated based on the spatial extent of the segmented surface data. This rectangular bounding box is translated along the directional information of the spine towards an adjacent spinal level. The translation distance is derived based on the size of the rectangular bounding box. The translated bounding box is used to segment the adjacent spinal level, resulting in an adjacent segmented surface data.

The segmented surface data is registered to the adjacent segmented surface data via a surface registration algorithm, to obtain the inter-level registration transform. The inter-level registration transform is stored in the system's memory.

The three volumetric fiducials are transformed to the adjacent spinal level. As the fiducials may not necessarily lie on the surface of the adjacent segmented surface data, the fiducials are then brought to the surface by nearest neighbor search. These adjacent volumetric fiducial points are stored in the system's memory. The adjacent volumetric fiducial points are used to segment the adjacent surface data, using them as seed points, and performing region growing. The refined adjacent segmented surface data is stored in the system's memory.

According to the present non-limiting example method, the above steps of deriving the refined adjacent segmented surface data, adjacent volumetric fiducial points, and inter-level registration transforms are performed for multiple spinal levels above and below the pre-selected spinal level in a sequential manner, which are stored in the system's memory.

If the volumetric image data was acquired before a surgery, all the processing steps above can be performed preoperatively.

During the surgery, when bony spinal structured have been exposed, a structured light imaging system is used to acquire an intraoperative surface data.

Using a tracked instrument, the user selects fiducials corresponding to the three volumetric fiducials on the patient, at the spinal level which they believe to correspond to the pre-selected spinal level. These intraoperative fiducial points are stored in the system's memory.

A registration is performed between the segmented surface data corresponding to the pre-selected spinal level and the spinal level selected intraoperatively, using the fiducials and segmented surface data. The mean, standard deviation of the registration error, and the number of matched points are recorded. These registration quality measures are stored in the system's memory.

A registration is similarly performed for all adjacent segmented surface data to the segmented surface data corresponding to the pre-selected spinal level. Registration quality measures, such as the mean, standard deviation of the registration error, and the number of matched points, are recorded. These registration quality measures are stored in the system's memory.

The registration quality measures are compared to determine whether the intraoperatively selected spinal level corresponds to the pre-selected spinal level on the volumetric data. For example, if all metrics independently support the choice of an intraoperative spinal level that corresponds to a pre-selected or adjacent spinal level, the choice would be communicated to the user with high confidence. Alternatively, if there are conflicting metrics, the conflicting metrics' ratios are compared. The metric from which a largest ratio is determined would be used for level suggestion, however, with lower confidence. In the event where conflicting metrics do not clearly suggest a particular spinal level, this too would be communicated to the user.

The specific embodiments described above have been shown by way of example, and it should be understood that these embodiments may be susceptible to various modifications and alternative forms. It should be further understood that the claims are not intended to be limited to the Therefore what is claimed is:

1. A method of performing intraoperative spinal level verification, the method comprising:

obtaining volumetric image data pertaining to a plurality of spinal levels of a spine;

processing the volumetric image data to generate multi-level surface data characterizing a bone surface of the spine;

obtaining input identifying at least three volumetric fiducial points at a pre-selected set of one or more contiguous spinal levels within a volumetric frame of reference associated with the volumetric image data and the multi-level surface data;

obtaining directional information associated with an orientation of the spine in the volumetric frame of reference;

employing at least one of the volumetric fiducial points to perform segmentation on the multi-level surface data, thereby obtaining segmented surface data associated with the pre-selected set of one or more contiguous spinal levels;

employing the directional information to determine an adjacent volumetric region within the volumetric frame of reference that is associated with an adjacent set of one or more contiguous spinal levels that is adjacent to the pre-selected set of one or more contiguous spinal levels;

performing segmentation on the multi-level surface data within the adjacent volumetric region, thereby obtaining adjacent segmented surface data associated with the adjacent set of one or more contiguous spinal levels;

registering the segmented surface data associated with the pre-selected set of one or more contiguous spinal levels to the adjacent segmented surface data, thereby obtaining an inter-level registration transform between the pre-selected set of one or more contiguous spinal levels and the adjacent set of one or more contiguous spinal levels;

intraoperatively detecting, with a surface detection subsystem, intraoperative surface data characterizing a surface region including at least a portion of an intraoperatively selected set of one or more contiguous spinal levels;

obtaining input identifying at least three intraoperative fiducial points associated with the intraoperatively selected set of one or more contiguous spinal levels, within an intraoperative frame of reference associated with the intraoperative surface data, each intraoperative fiducial point corresponding to a respective volumetric fiducial point;

employing the volumetric fiducial points and the corresponding intraoperative fiducial points to perform an initial registration between the segmented surface data and the intraoperative surface data, and performing a secondary surface-to-surface registration between the segmented surface data and the intraoperative surface data;

employing the inter-level registration transform to perform registration between the intraoperative surface data and the adjacent segmented surface data;

determining registration quality measures comprising:

a primary registration quality measure associated with a quality of the registration between the intraoperative surface data and the segmented surface data; and an adjacent registration quality measure associated with a quality of the registration between the intraoperative surface data and the adjacent segmented surface data associated with the adjacent set of one or more contiguous spinal levels; and providing feedback associated with the registration quality measures.

2. The method according to claim 1 wherein the feedback is suitable for inferring whether or not the intraoperatively selected set of one or more contiguous spinal levels is likely to correspond to the pre-selected set of one or more contiguous spinal levels.

3. The method according to claim 1 wherein the adjacent set of one or more contiguous spinal levels is a first adjacent set of one or more contiguous spinal levels, and wherein an additional adjacent registration quality measure is also determined for a second adjacent set of one or more contiguous spinal levels that is adjacent to the pre-selected set of one or more contiguous spinal levels and is located on an opposite side of the pre-selected set of one or more contiguous spinal levels relative to the first adjacent set of one or more contiguous spinal levels.

4. The method according to claim 1 further comprising:

generating additional adjacent segmented surface data associated with an additional adjacent set of one or more contiguous spinal levels, wherein the additional adjacent set of one or more contiguous spinal levels is adjacent to the adjacent set of one or more contiguous spinal levels having the adjacent segmented surface data associated therewith;

registering the adjacent segmented surface data associated with the adjacent set of one or more contiguous spinal levels to the additional adjacent segmented surface data associated with the additional adjacent set of one or more contiguous spinal levels, thereby obtaining an additional inter-level registration transform between the adjacent set of one or more contiguous spinal levels and the additional adjacent set of one or more contiguous spinal levels;

employing the additional inter-level registration transform to perform registration between the intraoperative surface data and the additional adjacent segmented surface data;

determining an additional registration quality measure characterizing a quality of the registration between the intraoperative surface data and the additional adjacent segmented surface data.

5. The method according to claim 4 wherein the additional adjacent segmented surface data is determined by:

employing the adjacent segmented surface data and the directional information to determine an additional adjacent volumetric region associated with the additional adjacent set of one or more contiguous spinal levels; and performing segmentation on the multi-level surface data within the additional adjacent volumetric region, thereby obtaining the additional adjacent segmented surface data associated with the additional adjacent set of one or more contiguous spinal levels.

6. The method according to claim 5 wherein a size of the additional adjacent volumetric region is determined by processing the adjacent segmented surface data to determine a spatial extent of the adjacent set of one or more contiguous spinal levels.

7. The method according to claim 4 wherein the additional adjacent segmented surface data is determined by:

applying the additional inter-level registration transform to one or more of the adjacent volumetric fiducial points, thereby obtaining one or more estimated additional adjacent volumetric fiducial locations associated with the additional adjacent set of one or more contiguous spinal levels;

employing the one or more estimated additional adjacent volumetric fiducial locations to determine one or more additional adjacent volumetric fiducial points associated with the additional adjacent set of one or more contiguous spinal levels; and performing region growing on the multi-level surface data relative to one or more of the additional adjacent volumetric fiducial points.

8. The method according to claim 1 further comprising, in the event that the primary registration quality measure is not a highest registration quality measure, providing feedback indicating that the intraoperatively selected set of one or more contiguous spinal levels may not correspond to the pre-selected set of one or more contiguous spinal levels.

9. The method according to claim 8 further comprising employing the inter-level registration transform to perform segmentation of the intraoperative surface data within a region corresponding to an adjacent intraoperative set of one or more contiguous spinal levels that is adjacent to the intraoperatively selected set of one or more contiguous spinal levels, thereby obtaining segmented adjacent intraoperative surface data, and employing registration between the segmented adjacent intraoperative surface data and segmented surface data associated with one or more of spinal levels of the volumetric image data in order to improve an accuracy of the feedback.

10. The method according to claim 8 further comprising:
obtaining input identifying at least three additional intraoperative fiducial points associated with an adjacent intraoperative set of one or more contiguous spinal levels that is adjacent to the intraoperatively selected set of one or more contiguous spinal levels;

employing the volumetric fiducial points and the corresponding additional intraoperative fiducial points to perform an initial registration between the segmented surface data and the intraoperative surface data, and performing a secondary surface-to-surface registration between the segmented surface data and the intraoperative surface data;

determining a supplementary registration quality measure associated with a quality of the registration between the intraoperative surface data and the segmented surface data, where the registration is based on the use of the at least three additional intraoperative fiducial points; and providing additional feedback suitable for inferring whether or not the adjacent intraoperative set of one or more contiguous spinal levels is likely to correspond to the pre-selected set of one or more contiguous spinal levels.

11. The method according to claim 1 further comprising, in the event that the primary registration quality measure is not a highest registration quality measure, providing feedback identifying an alternative intraoperative set of one or more contiguous spinal levels that is estimated to correspond to the pre-selected set of one or more contiguous spinal levels.

12. The method according to claim 11 further comprising:
obtaining input identifying at least three additional intraoperative fiducial points associated with the alternative intraoperative set of one or more contiguous spinal levels;

employing the volumetric fiducial points and the corresponding additional intraoperative fiducial points to perform an initial registration between the segmented surface data and the intraoperative surface data, and performing a secondary surface-to-surface registration between the segmented surface data and the intraoperative surface data;

determining a supplementary registration quality measure associated with a quality of the registration between the intraoperative surface data and the segmented surface data, where the registration is based on the use of the at least three additional intraoperative fiducial points; and providing additional feedback suitable for inferring whether or not the alternative intraoperative set of one or more contiguous spinal levels is likely to correspond to the pre-selected set of one or more contiguous spinal levels.

13. The method according to claim 11 further comprising:
identifying an inter-level registration transform corresponding to the set of one or more contiguous spinal levels in the volumetric image data that is associated with a largest registration quality measure;

employing the identified inter-level registration transform to determine additional intraoperative fiducial points within the intraoperative surface data;

employing the identified inter-level registration transform to transform the intraoperative fiducial points, thereby obtaining additional intraoperative fiducial points within the intraoperative surface data that correspond to the alternative intraoperative set of one or more contiguous spinal levels;

determining a supplementary registration quality measure associated with a quality of the registration between the intraoperative surface data and the segmented surface data, where the registration is based on the use of the at least three additional intraoperative fiducial points to perform an initial registration, followed by surface-to-surface registration; and providing additional feedback suitable for inferring whether or not the alternative intraoperative set of one or more contiguous spinal levels is likely to correspond to the pre-selected set of one or more contiguous spinal levels.

14. The method according to claim 1 wherein registration between the intraoperative surface data and the adjacent segmented surface data of the adjacent set of one or more contiguous spinal levels is performed by:
applying the inter-level registration transform between the pre-selected set of one or more contiguous spinal levels and the adjacent set of one or more contiguous spinal levels to the volumetric fiducial points, thereby obtaining estimated adjacent volumetric fiducial locations associated with the adjacent set of one or more contiguous spinal levels;

employing the estimated adjacent volumetric fiducial locations to determine adjacent volumetric fiducial points residing within an adjacent segmented surface defined by the adjacent segmented surface data; and employing the adjacent volumetric fiducial points and the corresponding intraoperative fiducial points to perform an initial registration between the adjacent segmented surface data of the adjacent set of one or more contiguous spinal levels and the intraoperative surface data, and performing a secondary surface-to-surface registration.

15. The method according to claim 1 wherein registration between the intraoperative surface data and the adjacent segmented surface data of a given adjacent set of one or more contiguous spinal levels is performed by:
applying, to the adjacent segmented surface data of the adjacent set of one or more contiguous spinal levels:
the inter-level registration transform between the pre-selected set of one or more contiguous spinal levels and the adjacent set of one or more contiguous spinal levels, for aligning the adjacent segmented surface data with the segmented surface data of the pre-selected set of one or more contiguous spinal levels; and
a volumetric-to-intraoperative registration transform determined when registering the segmented surface data to the intraoperative surface data, for aligning the adjacent segmented surface data with the intraoperative surface data, thereby obtaining transformed adjacent segmented surface data; and
performing registration between the segmented surface data and the transformed adjacent segmented surface data.

16. The method according to claim 1 wherein the directional information is determined employing one of: a DICOM header, principal component analysis, and spinal cord location extraction via image processing.

17. The method according to claim 1 wherein the directional information is determined by:
a) determining a preferential axis for processing the volumetric image data;
b) segmenting the volumetric image data into a series of volumetric slab segments arranged along the preferential axis;
c) identifying a volumetric slab segment containing at least one of the volumetric fiducial points;
d) determining an initial volumetric test region bounding the at least one of the volumetric fiducial points within the volumetric slab segment;
e) determining a center of mass location within the initial volumetric test region;
f) determining, based on the center of mass location, an adjacent volumetric test region within an adjacent volumetric slab segment, and determining an adjacent center of mass location within the adjacent volumetric test region;
g) repeating step f) one or more times to obtain a set of center of mass locations corresponding to different volumetric slab segments; and
h) processing the set of center of mass locations to determine the directional information characterizing the orientation of the spine.

18. The method according to claim 17 wherein when repeating step f) to identify an additional adjacent center of mass location within an additional adjacent volumetric slab segment, an additional adjacent volumetric test region within the additional adjacent volumetric slab segment is determined by translating a previously determined adjacent volumetric test region along a local axis, wherein the local axis is determined based on two center of mass locations corresponding to volumetric slab segments neighbouring the additional adjacent volumetric slab segment.

19. The method according to claim 17 wherein, when performing steps e) or f), the center of mass location that is determined is an estimated center of mass location, the method further comprising: (i) generating a refined center of mass location by determining a second volumetric test region bounding the estimated center of mass location, and (ii) determining the refined center of mass location within the second volumetric test region.

20. The method according to claim 19 further comprising repeating steps (i) and (ii) one or more times until a pre-selected convergence criterion has been satisfied.

21. The method according to claim 1 wherein one or more of the segmented surface data and the adjacent segmented surface data is obtained by performing region growing on the multi-level surface data.

22. The method according to claim 1 wherein the adjacent volumetric region associated with the adjacent set of one or more contiguous spinal levels is determined by:
determining a bounding box associated with the segmented surface data;
employing the directional information to translate the bounding box to a spatial region expected to contain the adjacent set of one or more contiguous spinal levels.

23. The method according to claim 1 wherein one or more of the intraoperative fiducial points are employed to segment the intraoperative surface data prior to performing registration.

24. The method according to claim 1 wherein the input identifying the at least three volumetric fiducial points at the pre-selected set of one or more contiguous spinal levels identifies the at least three volumetric fiducial points within the multi-level surface data.

25. The method according to claim 1 wherein the surface detection subsystem is a structured light subsystem.

26. A system for performing intraoperative spinal level verification, the system comprising:
a surface detection subsystem; and
computer hardware operatively coupled to said surface detection subsystem, wherein said computer hardware comprises memory coupled with one or more processors to store instructions, which when executed by the one or more processors, causes the one or more processors to perform operations comprising:
processing volumetric image data pertaining to a plurality of spinal levels of a spine to generate multi-level surface data characterizing a bone surface of the spine;
receiving input identifying at least three volumetric fiducial points at a pre-selected set of one or more contiguous spinal levels within a volumetric frame of reference associated with the volumetric image data and the multi-level surface data;
obtaining directional information associated with an orientation of the spine in the volumetric frame of reference;
employing at least one of the volumetric fiducial points to perform segmentation on the multi-level surface data, thereby obtaining segmented surface data associated with the pre-selected set of one or more contiguous spinal levels;
employing the directional information to determine an adjacent volumetric region within the volumetric frame of reference that is associated with an adjacent set of one or more contiguous spinal levels that is adjacent to the pre-selected set of one or more contiguous spinal levels;
performing segmentation on the multi-level surface data within the adjacent volumetric region, thereby obtaining adjacent segmented surface data associated with the adjacent set of one or more contiguous spinal levels;

registering the segmented surface data associated with the pre-selected set of one or more contiguous spinal levels to the adjacent segmented surface data, thereby obtaining an inter-level registration transform between the pre-selected set of one or more contiguous spinal levels and the adjacent set of one or more contiguous spinal levels;

controlling said surface detection subsystem to intraoperatively detect intraoperative surface data characterizing a surface region including at least a portion of an intraoperatively selected set of one or more contiguous spinal levels;

receiving input identifying at least three intraoperative fiducial points associated with the intraoperatively selected set of one or more contiguous spinal levels, within an intraoperative frame of reference associated with the intraoperative surface data, each intraoperative fiducial point corresponding to a respective volumetric fiducial point;

employing the volumetric fiducial points and the corresponding intraoperative fiducial points to perform an initial registration between the segmented surface data and the intraoperative surface data, and performing a secondary surface-to-surface registration between the segmented surface data and the intraoperative surface data;

employing the inter-level registration transform to perform registration between the intraoperative surface data and the adjacent segmented surface data;

determining registration quality measures comprising:
a primary registration quality measure associated with a quality of the registration between the intraoperative surface data and the segmented surface data; and
an adjacent registration quality measure associated with a quality of the registration between the intraoperative surface data and the adjacent segmented surface data associated with the adjacent set of one or more contiguous spinal levels; and
providing feedback associated with the registration quality measures.

27. A method of performing intraoperative spinal level verification, the method comprising:
obtaining volumetric image data pertaining to a plurality of spinal levels of a spine;
processing the volumetric image data to generate multi-level surface data characterizing a bone surface of the spine;
performing segmentation on the multi-level surface data, thereby obtaining:
segmented surface data associated with a pre-selected set of one or more contiguous spinal levels; and
adjacent segmented surface data associated with an adjacent set of one or more contiguous spinal levels;
intraoperatively detecting, with a surface detection subsystem, intraoperative surface data characterizing a surface region including at least a portion of an intraoperatively selected set of one or more contiguous spinal levels;
performing registration between the intraoperative surface data and the segmented surface data;
performing registration between the intraoperative surface data and the adjacent segmented surface data;
determining registration quality measures comprising:
a primary registration quality measure associated with a quality of the registration between the intraoperative surface data and the segmented surface data; and
an adjacent registration quality measure associated with a quality of the registration between the intraoperative surface data and the adjacent segmented surface data associated with the adjacent set of one or more contiguous spinal levels; and
providing feedback associated with the registration quality measures.

28. A system for performing intraoperative spinal level verification, the system comprising:
a surface detection subsystem; and
computer hardware operatively coupled to said surface detection subsystem, wherein said computer hardware comprises memory coupled with one or more processors to store instructions, which when executed by the one or more processors, causes the one or more processors to perform operations comprising:
processing volumetric image data pertaining to a plurality of spinal levels of a spine to generate multi-level surface data characterizing a bone surface of the spine;
performing segmentation on the multi-level surface data, thereby obtaining:
segmented surface data associated with a pre-selected set of one or more contiguous spinal levels; and
adjacent segmented surface data associated with an adjacent set of one or more contiguous spinal levels;
intraoperatively detecting, with said surface detection subsystem, intraoperative surface data characterizing a surface region including at least a portion of an intraoperatively selected set of one or more contiguous spinal levels;
performing registration between the intraoperative surface data and the segmented surface data;
performing registration between the intraoperative surface data and the adjacent segmented surface data;
determining registration quality measures comprising:
a primary registration quality measure associated with a quality of the registration between the intraoperative surface data and the segmented surface data; and
an adjacent registration quality measure associated with a quality of the registration between the intraoperative surface data and the adjacent segmented surface data associated with the adjacent set of one or more contiguous spinal levels; and
providing feedback associated with the registration quality measures.

* * * * *